(12) United States Patent
Long et al.

(10) Patent No.: US 7,907,699 B2
(45) Date of Patent: Mar. 15, 2011

(54) RADIOTHERAPEUTIC APPARATUS

(75) Inventors: Andrew Long, Leatherhead (GB); Michael Vogele, Schwabmünchen (DE)

(73) Assignee: Elekta AB (publ), Stockholm (SE)

( * ) Notice: Subject to any disclaimer, the term of this patent is extended or adjusted under 35 U.S.C. 154(b) by 51 days.

(21) Appl. No.: 12/281,093

(22) PCT Filed: Feb. 26, 2007

(86) PCT No.: PCT/EP2007/001618
§ 371 (c)(1),
(2), (4) Date: Jan. 28, 2009

(87) PCT Pub. No.: WO2007/098899
PCT Pub. Date: Sep. 7, 2007

(65) Prior Publication Data
US 2009/0238338 A1   Sep. 24, 2009

(30) Foreign Application Priority Data
Feb. 28, 2006   (GB) .................................. 0603970.5

(51) Int. Cl.
*A61N 5/10* (2006.01)
(52) U.S. Cl. ........................................................ 378/65
(58) Field of Classification Search .................... 378/18, 378/65, 207, 20, 205
See application file for complete search history.

(56) References Cited

U.S. PATENT DOCUMENTS

| | | | |
|---|---|---|---|
| 5,745,545 A * | 4/1998 | Hughes | 378/65 |
| 5,769,861 A | 6/1998 | Vilsmeier | |
| 5,799,059 A | 8/1998 | Stembridge et al. | |
| 5,820,553 A * | 10/1998 | Hughes | 600/426 |
| 6,118,848 A * | 9/2000 | Reiffel | 378/65 |
| 6,493,574 B1 * | 12/2002 | Ehnholm et al. | 600/429 |
| 6,527,443 B1 | 3/2003 | Vilsmeier | |
| 6,535,574 B1 * | 3/2003 | Collins et al. | 378/65 |
| 6,585,412 B2 * | 7/2003 | Mitschke | 378/207 |
| 6,626,569 B2 * | 9/2003 | Reinstein et al. | 378/206 |

(Continued)

FOREIGN PATENT DOCUMENTS

DE   10231630 A1   1/2004

(Continued)

OTHER PUBLICATIONS

PCT International Search Report, Jan. 18, 2008.

(Continued)

*Primary Examiner* — Allen C. Ho
(74) *Attorney, Agent, or Firm* — Z. Peter Sawicki; Westman, Champlin & Kelly, P.A.

(57) ABSTRACT

A reference phantom includes CT-imageable detail together with light-reflective spheres. This item can be placed on a patient table in a known location, following which the diagnostic source can be activated to detect the phantom position relative to the isocentre and camera employed to detect the PSS position. A synthetic image of the phantom can be used for comparison with the CT dataset. This allows improved correlation of the source and the patient support, enable further steps to be taken in enhancing the clinical effectiveness of the apparatus. In-use variations of the isocentre location can be corrected in real time by adjustment of the patient support. Thus, as the isocentre moves, the patient can be moved so as to track the moving isocentre. The linac arm could also be designed differently, as the existing design constraint (that isocentre movement must be limited as far as possible) could potentially be relaxed in order to achieve other aims.

6 Claims, 2 Drawing Sheets

U.S. PATENT DOCUMENTS

| | | | |
|---|---|---|---|
| 6,842,502 B2 * | 1/2005 | Jaffray et al. | 378/65 |
| 6,865,253 B2 * | 3/2005 | Blumhofer et al. | 378/65 |
| 6,974,254 B2 * | 12/2005 | Paliwal et al. | 378/207 |
| 7,010,095 B2 * | 3/2006 | Mitschke et al. | 378/162 |
| 7,356,120 B2 * | 4/2008 | Main et al. | 378/65 |
| 7,594,753 B2 * | 9/2009 | Main et al. | 378/207 |
| 7,613,501 B2 * | 11/2009 | Scherch | 600/427 |
| 7,715,606 B2 * | 5/2010 | Jeung et al. | 382/128 |
| 7,756,244 B2 * | 7/2010 | Mostafavi | 378/20 |
| 2003/0048868 A1 | 3/2003 | Bailey et al. | |
| 2004/0068169 A1 | 4/2004 | Mansfield et al. | |

FOREIGN PATENT DOCUMENTS

| | | |
|---|---|---|
| DE | 102004048066 A1 | 4/2006 |
| WO | 9927839 A | 6/1999 |
| WO | 0235454 A | 5/2002 |
| WO | 03039212 A | 5/2003 |
| WO | 2006062872 A | 6/2006 |

OTHER PUBLICATIONS

UK Search Report, Jun. 1, 2006.

* cited by examiner

RADIOTHERAPEUTIC APPARATUS

CROSS-REFERENCE TO RELATED APPLICATION

This Application is a Section 371 National Stage Application of International Application No. PCT/EP2007/001618, filed Feb. 26, 2007 and published as WO 2007/098899A2 and WO 2007/098899 A3 on Sep. 7, 2007, the content of which is hereby incorporated by reference in its entirety.

FIELD OF THE INVENTION

The present invention relates to radiotherapeutic apparatus.

BACKGROUND ART

In general, radiotherapy treatment systems involve a source of ionising radiation, such as a linear accelerator, and a patient support system (PSS) on which the patient can be placed, in the field of view of the source.

The source is rotateable around the PSS so that a radiation dose can be applied to the patient from a number of directions in order to minimise the dose applied to healthy tissue, and the intersection of the axis of rotation with the beam centreline defines the "isocentre". The PSS is moveable so as to assist in aligning the patient with the isocentre; in general a clinician will wish to place the tumour at the isocentre, although this may not always be the case. Given that the source and the PSS are both moveable, it will be necessary to ensure that they are both aligned to the same frame of reference so that the clinician can be confident that the patient is indeed in the correct position.

A modern PSS is moveable in up to six degrees of freedom with a high degree of accuracy, these being translation in three directions, rotation about a vertical axis, and tilting in two directions. To calibrate this, a reference frame can be affixed to the PSS surface, which has reflective spheres in a known and asymmetric arrangement. These are viewed by an infrared camera and the image is analysed. Given that the arrangement of the spheres is known a priori, the orientation of the reference frame and hence the table can be determined.

The source commonly includes both a therapeutic beam and a correlated diagnostic beam. A flat panel imager is placed opposite the diagnostic beam to obtain an image, and this can be used during the treatment process to image the tumour and update its position. During calibration, the return from the diagnostic imager can be used to identify the isocentre location.

It therefore remains only to correlate the two sets of location data. To do so, laser calibration beams directed at the isocentre have hitherto been used. These illuminate the isocentre and therefore make it visible, allowing the reference frame to be aligned with the isocentre by moving the PSS, after which the frame location is determined via the camera system. Thus, the PSS frame of reference is calibrated relative to the isocentre.

SUMMARY OF THE INVENTION

There are a number of problems in this approach. One such problem is that the correlation is not direct, i.e. the total error in determining the reference frame position and the isocentre will also include the error in aligning the lasers to the believed spatial location of the isocentre and the error in that spatial location as compared to the actual location of the isocentre. The uncertainty in the location to which the dose is being applied is equal to the total of all these errors. That uncertainty represents a limitation on the clinical effectiveness of the device when treating tumours that are near to sensitive areas, such as prostate cancer, since a margin corresponding to that error must be left around the treatment area.

The present invention therefore provides a reference phantom that includes CT-imageable detail together with light-reflective spheres. This item can be placed on the PSS in a known location, following which the diagnostic source can be activated to detect the phantom position relative to the actual isocentre (as observed by the beam) and the camera employed to detect the PSS position. This will completely eliminate the above source of error since the same object will be used as the reference point for both frames of reference.

The CT-imageable detail can be as simple as one or more bores, protrusions or formations formed in or on a substrate that is otherwise partially absorptive of x-radiation. A plurality of such bores will be preferable, as these can be arranged in an orientation that is rotationally asymmetric. Then, from the CT image it will be possible to derive a unique orientation for the phantom. However, a single bore, protrusion or formation that is itself rotationally asymmetric or such an element in an asymmetric location on the phantom will achieve the same end. It is to be noted that simple cylindrical bores are easiest to form in practice.

The isocentre is located relative to the phantom by analysing the data from the diagnostic imager relative to the expected position of the phantom. This requires that the system knows a priori the expected image, and this is easiest done by imaging the phantom via an existing system to obtain a 3 dimensional CT volume image that can be compared to the output of the diagnostic system.

However, we prefer to give the system a synthetic image of the phantom. By this, we mean an image that has been calculated from the known dimensions and absorption properties of the phantom. Such an image will be sharper than any CT system could deliver since it will correspond to the image from a theoretically perfect imaging system. In the process of comparison between the two image sets, there will be less uncertainty over (for example) the location of the object edge since one edge (of the two being compared) will be localised precisely, such as to the edge of one voxel.

These enhancements to the correlation of the source and the PSS enable further steps to be taken in enhancing the clinical effectiveness of the apparatus. In practice, the isocentre is not actually fixed. As the source rotates, the direction of the earth's magnetic field relative to the apparatus rotates (relative to the source) accordingly. As an artificial magnetic field is used to direct the beam of electrons to the x-ray target to produce a beam, the beam will be deflected, albeit by a small amount. In addition, the therapeutic source is very heavy, and its weight will act in a different direction relative to the linac arm on which it is supported as it is rotated. This will likewise cause the beam to move. Therefore, the isocentre location is in fact a function of the source angle.

The calibration lasers are necessarily fixed, and therefore there has hitherto been a need to take care to minimise movement of the isocentre. In practice, an isocentre volume has been defined and care was taken to make this as small as possible, such as by strengthening the arm and shielding the accelerator from external magnetic fields.

Given that the isocentre is not actually a volume but is in fact a moving spot, the ability to calibrate the isocentre and the PSS together dynamically means both that this movement can be detected and that we can use the existing sub-millimeter accuracy of a modern PSS to compensate for isocentre movement. Thus, as the isocentre moves, the patient could be moved so as to track the moving isocentre. Even in a well-designed system with little isocentre movement, this will reduce the uncertainty in the isocentre location. This again means that less volume around the treatment area needs to be allowed for, allowing a more aggressive treatment of a tumour even near to a sensitive area. This, in turn, allows the same dose to be delivered in fewer iterations, thereby speeding treatment and reducing side-effects.

This could also allow the linac arm to be designed differently, as the existing design constraint (that isocentre movement must be limited as far as possible) could potentially be relaxed in order to achieve other aims.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
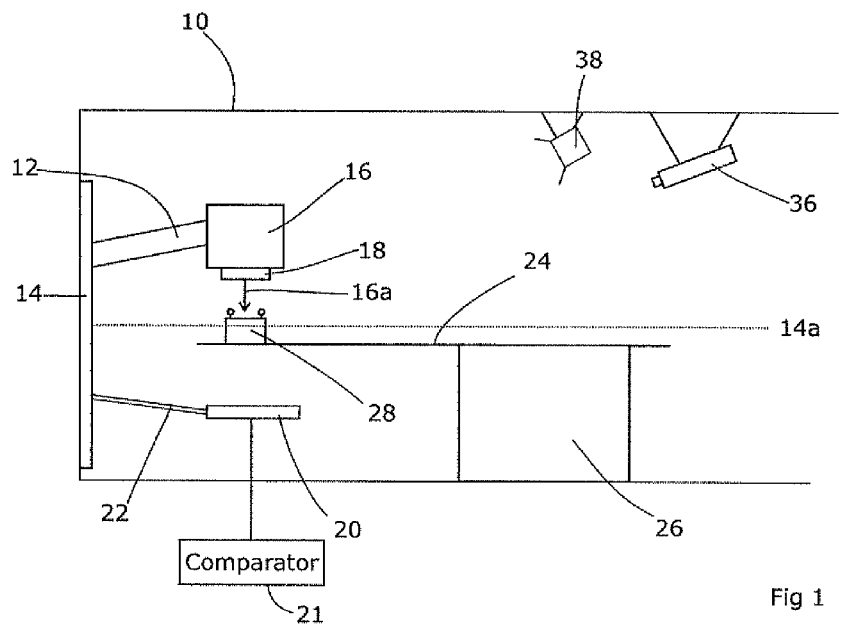
FIG. 1 shows a schematic view from one side of a linear accelerator (linac) and PSS being calibrated according to the present invention.

FIG. 1 shows a typical radiotherapy apparatus. A dedicated room 10 is fitted with a linear accelerator arm 12 which extends from a rotateable support 14 and ends with an x-ray head 16 for the production of therapeutic and/or diagnostic radiation. In this example, the x-ray head is adapted to produce radiation of a range of energies varying from kV energies suitable for diagnostic purposes to MV energies suitable for therapeutic use. This has the advantage that the two sources are inherently aligned in that they emanate from the same apparatus. A collimator set 18 is provided in order to shape the beam as required and contains aperture collimators, block collimators and multi-leaf collimators.

A flat panel imager 20 and a comparator 21 are provided, located on an extendable arm 22 attached to the rotateable support 14 at a location opposite the linear accelerator arm 12, i.e. spaced 180° therefrom. When the head 16 is producing low energy radiation, the imager 20 can detect the resulting image after absorption by the patient and produce the necessary data for cone-beam CT analysis. During therapeutic use, the extendable arm 22 can be withdrawn to remove the flat panel imager from the beam, or it can be left in place to produce portal images.

As the support 14 rotates about its centreline 14a, the beam 16a produced by the head 16 will address its point of intersection with the centreline 14a from a range of different angles. This point is usually referred to as the isocentre.

Figure 2:
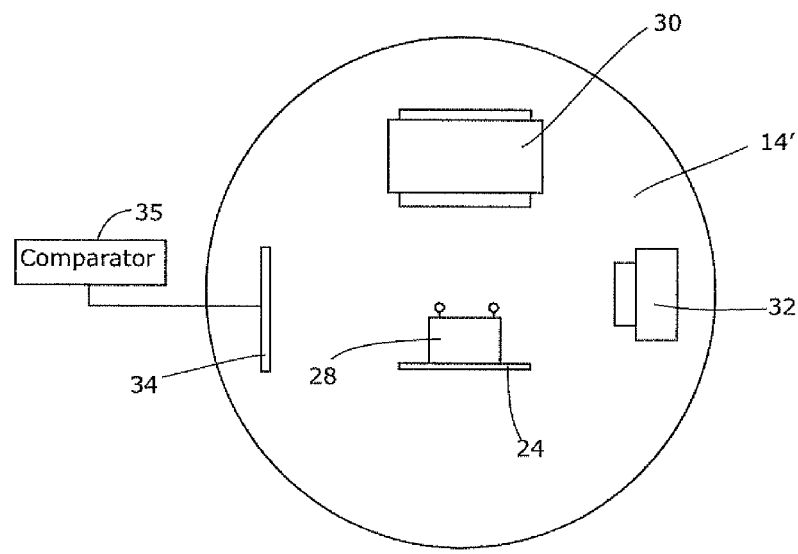
FIG. 2 shows a view along the linac rotation axis of an alternative apparatus.

An alternative form of apparatus employs separate therapeutic and diagnostic sources, typically mounted on the same rotateable support, separated by 90°. A flat panel imager is also provided for at least the diagnostic source and possibly also the therapeutic source. FIG. 2 shows such an arrangement with a therapeutic source 30, a diagnostic source 32, and a flat panel imager 34 all mounted on the same rotateable support 14'.

A comparator 35 is operably connected to the imager 24.

A patient table 24 is supported on an adjustable base 26. The base 26 includes servo motors arranged to move the table 24 in any of six degree of freedom, i.e. three linear directions and three rotation directions. In the calibration stage shown in FIG. 1, a phantom 28 is placed at the head of the table 24 and the table 24 is moved to place the phantom at (approximately) the isocentre.

A camera 36 is mounted on the ceiling with a view of the table 24 and, in particular, the isocentre. It therefore has a good view of the phantom 28. The camera can use any part of the visual spectrum but in this case is an infra-red camera. Suitable infra-red sources 38 can be disposed around the room if necessary, to illuminate the phantom 28.

Figure 3:
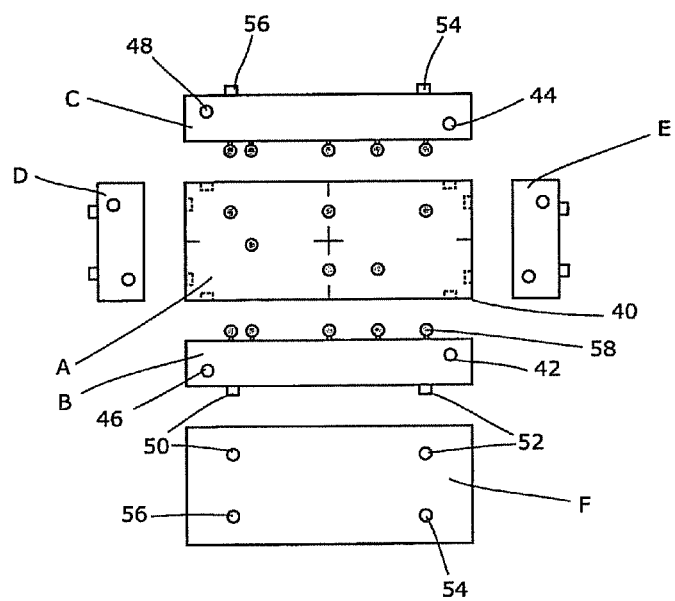
FIG. 3 shows views from each direction of the phantom according to the present invention.

FIG. 3 shows the phantom 28 in greater detail. Views are provided from each direction as follows;
A Top view
B Front side view
C Rear side view
D Left side view
E Right side view
F View from beneath Each view is oriented such that corresponding edges are adjacent so, for example, the lower edge of the rear side view C is the edge shown adjacent, the upper edge of the top view A.

Thus, the phantom 28 comprises a block 40 made of an acrylic polymer such as Poly(methyl methacrylate) sold under the trademark Perspex formed into an asymmetric shape. Perspex is advantageous in that it has suitable absorption properties for diagnostic x-rays, and will produce an image with adequate contrast. Likewise, it is easy to form by moulding, cutting and boring processes. In this example, the block 40 has been formed in a cuboid shape with an asymmetric pattern of bores. Each dimension of the block is different, and the bores are placed on the side faces in an arrangement that identifies specific ends. Thus, for example, the front and rear side faces each have a bore 42, 44 in their upper corner adjacent the right edge of the block, and a bore 46, 48 in their lower corner adjacent the left edge of the block. A like arrangement is provided for the left and right side faces.

Four protrusions 50, 52, 54, 56 are formed on the underside of the phantom 28. These lift the underside of the phantom 28 off the patient table 24, and allow the phantom to be distinguished by the CT system more easily, without confusion with the table.

Thus, the combination of different dimensions and bore locations allows the unique orientation of the phantom to be determined by a CT system.

The phantom also has a number of reflective spheres 58 arranged on the top surface. Each sphere 58 is attached to the block 40 by a short rod, to space the sphere from the block and allow better resolution of the sphere by the camera 36. As shown in view A, the spheres are disposed in an asymmetric pattern that, again, allows for unique recognition of the orientation of the phantom.

Thus, in use the phantom 28 is placed on the patient table 24 as shown in FIG. 1. The diagnostic source is activated, or the combined source set to produce diagnostic x-rays, and a CT scan of the phantom is prepared. The three-dimensional image that is produced is compared to a known image of the phantom in order to determine the orientation thereof. Given the asymmetries described above, the known image and the prepared image will only match in a single orientation.

The known image can of course be a previously prepared image of the phantom. However, for the advantages described above, we prefer to use a computer-generated image of the phantom, prepared using its known dimensions and absorption properties. In practice, these synthetic 3D images of the reference phantom are augmented with a synthetic treatment plan, which defines how the reference phantom is expected to be positioned with respect to the treatment geometry. Thus, the synthetic data describes the physical structure of the phantom, and also tells the diagnostic systems where the isocentre is expected to be located within that perfect phantom. By comparing the synthetic reference data (being the image data and a planned isocentre) with the actual measured data (being the scanned image and an isocentre calibrated by the diagnostic systems), we are able to locate the phantom within the treatment geometry and hence calibrate the patient support.

Further, the camera 36 is able to view the phantom 28 on the table 24 and, by virtue of the asymmetric arrangement of the spheres 58, the image can be analysed to yield the unique orientation of the phantom 28.

This means that the orientation of the phantom can be determined accurately and uniquely by both the camera and the CT system. Given that the CT is integral with the x-ray system and therefore the isocentre, and that the camera is fixed relative to the table base 26, this allows both systems to be brought into a single alignment.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A radiotherapeutic apparatus comprising a source of therapeutic radiation and a correlated source of diagnostic radiation, a detector for the diagnostic radiation, a CT imaging system for deriving a three-dimensional image from the detector, a moveable patient support system, a camera for viewing a location of the patient support system, a reference phantom including CT-imageable detail together with at least one light-reflective element and a comparator for output of the CT imaging system with an a priori image of the phantom thereby to determine an orientation of the phantom.

2. The radiotherapeutic apparatus according to claim 1 in which the a priori image is a previous image of such a phantom in a known orientation.

3. The radiotherapeutic apparatus according to claim 1 in which the a priori image is a synthetic image of the phantom.

4. The radiotherapeutic apparatus according to claim 1, including means for retaining a treatment plan consisting of at least one treatment parameter, wherein the a priori image of the phantom is calculated taking the at least one treatment parameter into account.

5. The radiotherapeutic apparatus according to claim 4 in which the at least one treatment parameter includes at least one of:
   a. a location of the patient support system relative to the source of therapeutic radiation
   b. an orientation of the source of therapeutic radiation relative to the patient support system;
   c. an orientation of the source of diagnostic radiation relative to the patient support system; and
   d. a location of the phantom relative to the source of therapeutic radiation.

6. A radiotherapeutic apparatus comprising a source of therapeutic radiation having an isocentre location, and a correlated source of diagnostic radiation, a detector for the diagnostic radiation, a CT imaging system for deriving a three-dimensional image from the detector, a moveable patient support system, a camera for viewing a location of the patient support system, and a control means arranged to adjust a position of the patient support system in synchrony with a known variation in the isocentre location wherein the source of therapeutic radiation is rotateable about an axis and the control system detects the rotational position thereof and infers a location for the isocentre location based on the detected rotational position.

* * * * *